(12) United States Patent
Fedegari et al.

(10) Patent No.: US 12,091,203 B2
(45) Date of Patent: Sep. 17, 2024

(54) APPARATUS FOR FILLING CONTAINERS IN A STERILE ENVIRONMENT

(71) Applicant: FEDEGARI AUTOCLAVI S.P.A., Pavia (IT)

(72) Inventors: Giuseppe Fedegari, Pavia (IT); Paolo Fedegari, Celerina/Schlarigna (CH)

(73) Assignee: FEDEGARI AUTOCLAVI S.P.A., Pavia (IT)

( * ) Notice: Subject to any disclaimer, the term of this patent is extended or adjusted under 35 U.S.C. 154(b) by 212 days.

(21) Appl. No.: 17/776,241

(22) PCT Filed: Nov. 27, 2020

(86) PCT No.: PCT/IB2020/061223
§ 371 (c)(1),
(2) Date: May 12, 2022

(87) PCT Pub. No.: WO2021/105948
PCT Pub. Date: Jun. 3, 2021

(65) Prior Publication Data
US 2022/0396386 A1    Dec. 15, 2022

(30) Foreign Application Priority Data
Nov. 29, 2019   (IT) .......................... 102019000022554

(51) Int. Cl.
*B65B 59/04*         (2006.01)
*A61L 2/18*          (2006.01)
(Continued)

(52) U.S. Cl.
CPC ................ *B65B 59/04* (2013.01); *A61L 2/18* (2013.01); *A61L 2/26* (2013.01); *B08B 3/04* (2013.01);
(Continued)

(58) Field of Classification Search
CPC ..... B65B 59/04; B65B 55/025; B65B 65/003; B65B 2210/06; A61L 2/18; A61L 2/26;
(Continued)

(56) References Cited

U.S. PATENT DOCUMENTS 6,761,191 B2 *   7/2004   Rosen .................... B67C 3/005
                                                  141/144
6,941,981 B2 *   9/2005   Rosen .................... B67C 3/001
                                                  141/85
(Continued)

FOREIGN PATENT DOCUMENTS

| CN | 107929764 A | 4/2018 |
| EP | 1561473 A1 | 8/2005 |

(Continued)

OTHER PUBLICATIONS

International search report and Written Opinion dated Nov. 27, 2020 in PCT/IB2020/061223 filed Nov. 29, 2019, 15 Pages.

*Primary Examiner* — Nicolas A Arnett
(74) *Attorney, Agent, or Firm* — Gearhart Law, LLC

(57) ABSTRACT

The present invention relates to an apparatus (10) for filling containers in a sterile environment, comprising a filling unit (40) configured to fill containers with sterilized liquids or powders in a sterile environment comprising interchangeable parts characteristic of each production run; a washer sterilizer (20) configured to wash, sterilize, decontaminate, dry in one single process said interchangeable parts of the filling unit (40) before each run for filling the unit (40). The washer sterilizer (20) is directly coupled to the filling unit (40) and is configured to aseptically transfer the interchangeable parts directly to the filling unit (40).

7 Claims, 7 Drawing Sheets

(51) Int. Cl.
*A61L 2/26* (2006.01)
*B08B 3/04* (2006.01)
*B08B 13/00* (2006.01)
*B65B 55/02* (2006.01)
*B65B 65/00* (2006.01)
*A61L 2/20* (2006.01)

(52) U.S. Cl.
CPC .............. *B08B 3/042* (2013.01); *B08B 13/00* (2013.01); *B65B 55/025* (2013.01); *B65B 65/003* (2013.01); *A61L 2/20* (2013.01); *A61L 2202/17* (2013.01); *B65B 2210/06* (2013.01)

(58) Field of Classification Search
CPC ......... A61L 2/20; A61L 2202/17; B08B 3/04; B08B 3/042; B08B 13/00
See application file for complete search history.

(56) References Cited

U.S. PATENT DOCUMENTS

| | | | | |
|---|---|---|---|---|
| 8,613,584 | B2* | 12/2013 | Trebbi | A61L 2/24 29/466 |
| 9,718,583 | B2* | 8/2017 | Nicoletti | B65D 65/02 |
| 11,208,227 | B2* | 12/2021 | Gigante | B65B 35/00 |
| 11,505,352 | B2* | 11/2022 | Hahn | B29C 49/48 |
| 2005/0166948 | A1* | 8/2005 | Monti | B08B 9/0321 134/115 R |
| 2005/0217752 | A1* | 10/2005 | Facchini | A61J 3/074 141/146 |
| 2009/0202335 | A1* | 8/2009 | Trebbi | A61L 2/07 414/801 |
| 2011/0214779 | A1* | 9/2011 | Goldman | B67C 3/026 426/240 |
| 2021/0009296 | A1* | 1/2021 | Olsen | A61L 2/12 |

FOREIGN PATENT DOCUMENTS

| | | |
|---|---|---|
| KR | 20060107034 A | 10/2006 |
| NO | 20171946 A1 | 6/2019 |
| WO | 2007113664 A2 | 10/2007 |
| WO | 2008121792 A2 | 10/2008 |

* cited by examiner

APPARATUS FOR FILLING CONTAINERS IN A STERILE ENVIRONMENT

The present application is a national phase application of a PCT Application No. PCT/IB2020/061223 filed on Nov. 27, 2020, which claims a priority to Italian Patent Application No. 102019000022554 filed in Italy on Nov. 29, 2019, disclosures of which are incorporated in their entireties by reference herein.

TECHNICAL FIELD OF THE INVENTION

The present invention relates in general to the sector of machinery operating in sterile environments for the production and packaging of sterile liquids or powders in containers. More in particular, the present invention relates to an apparatus for filling containers in a sterile environment, comprising a unit for treating machine parts of a filling line, in particular to ensure that they can be washed, sterilized and/or aseptically transferred or allow an aseptic transfer in an insulator, RABS ("Restricted Area Barrier System") or any other system which allows activity under controlled contamination conditions.

PRIOR ART

One of the steps of production of sterile liquids or powders in an aseptic environment is the filling of the final container with which the drug will be placed on the market. The final container may be a bottle, syringe, tube or the like.

Production lines operate in controlled contamination environments.

In particular, filling lines are protected by segregation systems which insulate the machinery itself from any contact with an operator (insulators, closed RABS and open RABS). Before beginning a production run, the filling line requires a set up.

In detail, it is a question of assembling the machine parts in the line which had been disassembled at the end of the previous run to be cleaned, washed, sterilized and/or to install the machine parts which must be replaced for the format change. In particular, the machine parts may be liquid container filling needles, feed systems, rubber stoppers, material storage reservoirs, powder dosing systems, and the like.

Among the known operations the following can be highlighted:
- the cleaning of the machinery to prevent the cross contamination of polluting residues from a previous run from compromising the next one (cross contamination");
- the assembly of line parts which must be changed and/or washed/sterilized before each production run.

These operations require a set of steps which must be carried out with qualified operators, validated procedures and the registration of the activities carried out.

A typical sequence for transferring machine parts within an insulator containing a filling line can be described synthetically starting from FIG. 1.

Before the start of each run, some removable parts of the filling line must be washed, sterilized and subsequently assembled in sequence.

As shown in FIG. 1, the parts are washed inside a washing machine 1.

After washing and before sterilization (inside an autoclave or sterilizer 2a) the removable parts are bagged (usually in an area 3 protected by a laminar flow) with a special material which allows to maintain the sterility conditions of the treated objects during the transfer from the autoclave to the line.

In particular, the material of the bags is impermeable to air and permeable to certain sterilizing agents.

The parts of the filling machine which have been sterilized and are protected by the bags are subsequently placed inside an insulator 4, accessible by passing through a pressurization buffer 6.

At this point, the doors of the insulator 4 are hermetically closed and the interior thereof is treated with a decontaminating agent (for example, with hydrogen peroxide vapours).

Once the decontamination cycle has been completed, the operators only act through gloves present in the insulator and no longer open the doors thereof until the completion of the run inside the filling line 5.

After the decontamination of the filling line 5, in order to begin production, the line 5 must still be equipped.

In this case, by acting with the gloves, the operators open the bags containing the treated pieces and mount them in the positions thereof inside the filling line 5.

The operations described above may vary in detail but not in the main sequences for any known type of line.

Some alternatives to the previous flow are illustrated in FIGS. 2 and 3.

In the first case (FIG. 2) the machinery pieces or parts are washed and sterilized with a single machine (washer sterilizer 2b).

In a first step the pieces are loaded from one side of the washer sterilizer 2b, washed, unloaded from the same side, bagged in the bagging unit 3, sterilized in the washer sterilizer 2b and subsequently transferred to the filling line 5 as described in the previous process. Another type of transfer can be carried out with the diagram shown in FIG. 3.

In this case the machine parts are washed and sterilized in a single cycle in the machine 2b.

At the end of this washing and sterilization, the sterilized load is transferred inside a transport unit 7. The transport unit 7 is made so that it can maintain the necessary aseptic conditions as well as the connection systems thereof with autoclave and line.

If instead of an insulator 4 the filling line 5 was protected by a RABS, the equipping operations of the line 5 would not change significantly.

The main difference is that if the line 5 is protected by a RABS, the decontamination of the same is carried out in conjunction with that of the room containing it.

The procedures described above (FIGS. 1 and 2) have the following disadvantages:
- a large number of operations to be performed;
- need for qualified personnel, procedures and records of each activity: the greater the number of operations to be performed, the greater the costs and the probability of an error;
- at least two distinct machines (washing machine and autoclave) and respective work areas to be kept in operation are required;
- need to bag the pieces.

The procedure illustrated in FIG. 2 also presents the following problems:
- identical complexity of operations of the case of FIG. 1;
- use of only one machine (i.e., washer sterilizer 2b), but in two distinct times;
- the production flow is interrupted and then resumed.

The procedure illustrated in FIG. 3 presents the following disadvantages:
- the need to bag the pieces is completely eliminated but a complex machine is introduced into the production process, i.e., the transport unit 7, for the transfer of the pieces from the washer sterilizer 2b to the filling line 5;
- the washer sterilizer 2b and the filling line 5 must be provided with connection systems which guarantee the necessary aseptic conditions of the transfer.

The object of the present invention is therefore to at least partially overcome the drawbacks, mentioned above with reference to the prior art, creating an apparatus for filling containers in a sterile environment, comprising a unit for treating machine parts of a filling line, in particular to ensure that they can be washed, sterilized and/or aseptically transferred or allow an aseptic transfer in an insulator, RABS ("Restricted Area Barrier System") or any other protection system which allows activity under controlled contamination conditions.

Another object of the present invention is that of providing an apparatus for filling containers in a sterile environment which can guarantee a high level of safety and sterility.

A further object of the present invention is that of providing an apparatus for filling containers in a sterile environment which is efficient.

A further and not least object of the present invention is that of providing an apparatus for filling containers in a sterile environment which is highly reliable, easy to obtain and simple to use.

BRIEF SUMMARY OF THE INVENTION

The present invention relates to an apparatus for filling containers in a sterile environment as defined in the accompanying claim 1 and the preferred embodiments thereof disclosed in dependent claims.

The Applicant has perceived that the apparatus for filling containers in a sterile environment in accordance with the present invention allows to obtain a smaller surface occupied by the machine, a reduction in process times and personnel costs used to reach a lower cost of process validation, staff training and maintenance on the machine.

Another advantage of the present invention relates to the safety and complete sterility of all pre-filling and post-filling operations of containers with sterile liquids and/or powders.

The technical effects/advantages mentioned, and other technical effects/advantages of the invention, will emerge in further detail from the description provided herein below of an example embodiment provided by way of approximate and non-limiting example with reference to the appended drawings.

BRIEF DESCRIPTION OF THE DRAWINGS

Additional features and advantages of the invention will become more apparent from the description which follows of a preferred embodiment and the variants thereof, provided by way of example with reference to the appended drawings, in which.

DETAILED DESCRIPTION OF THE INVENTION

It should be noted that in the description below, identical or similar blocks, components or modules, even if they appear in different embodiments of the invention, are indicated by the same numerical references in the figures.

Figure 1:
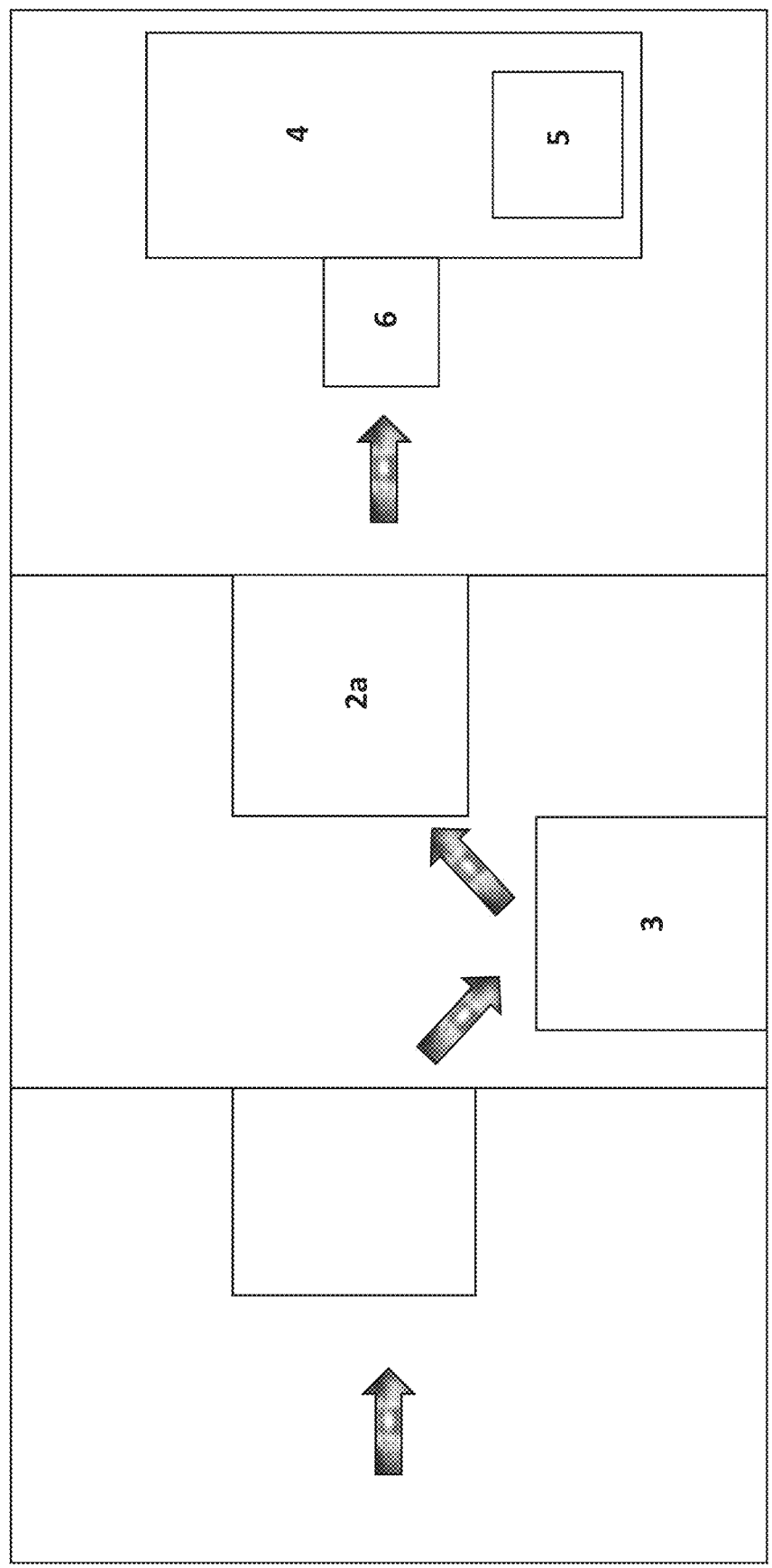
FIG. 1 shows a block diagram of a washing, sterilization and/or aseptic transfer treatment process of components of a container filling line according to the prior art.
Figure 2:
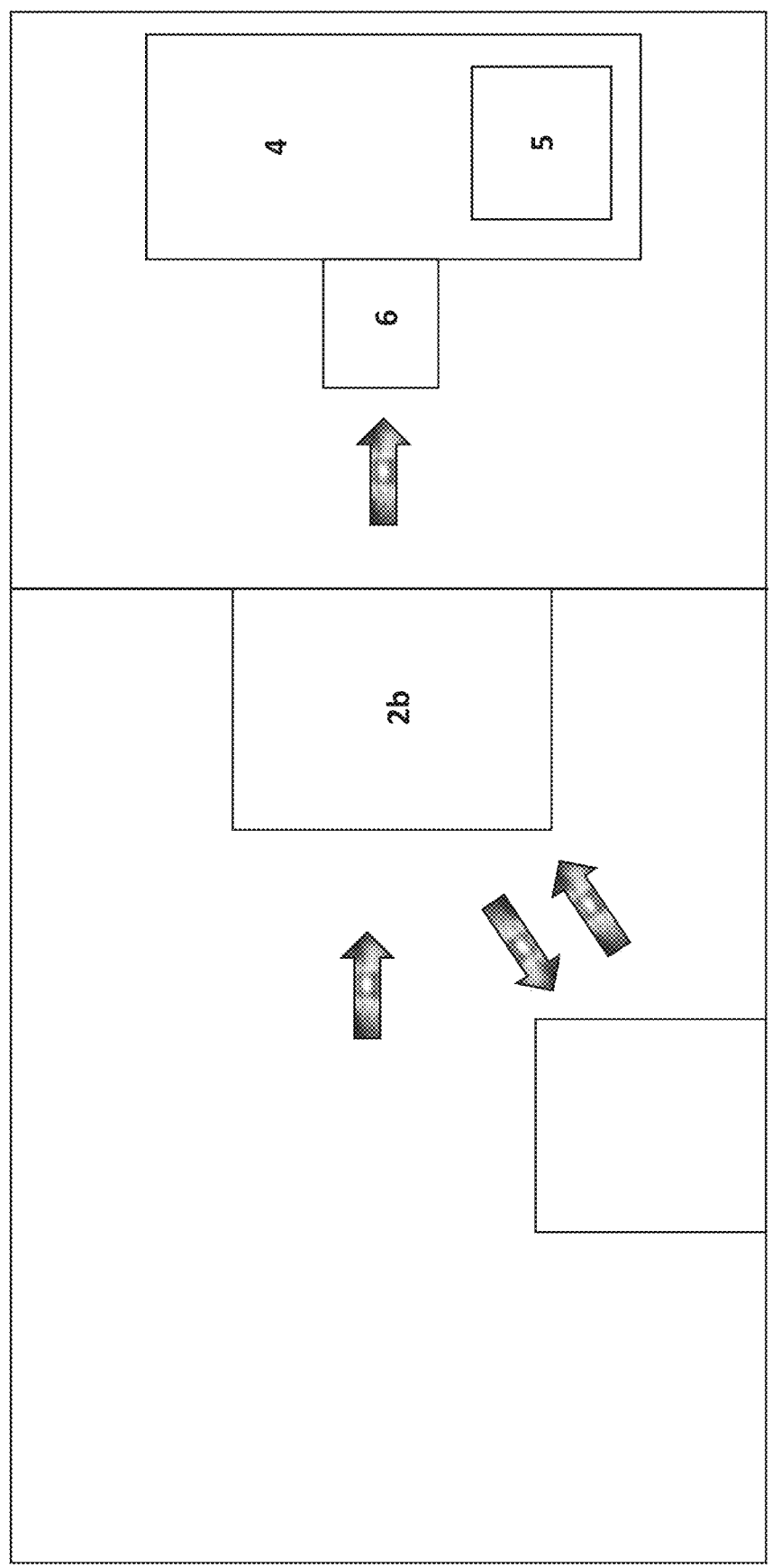
FIG. 2 shows a block diagram of a washing, sterilization and/or aseptic transfer treatment process of a known type of alternative to that of FIG. 1.
Figure 3:
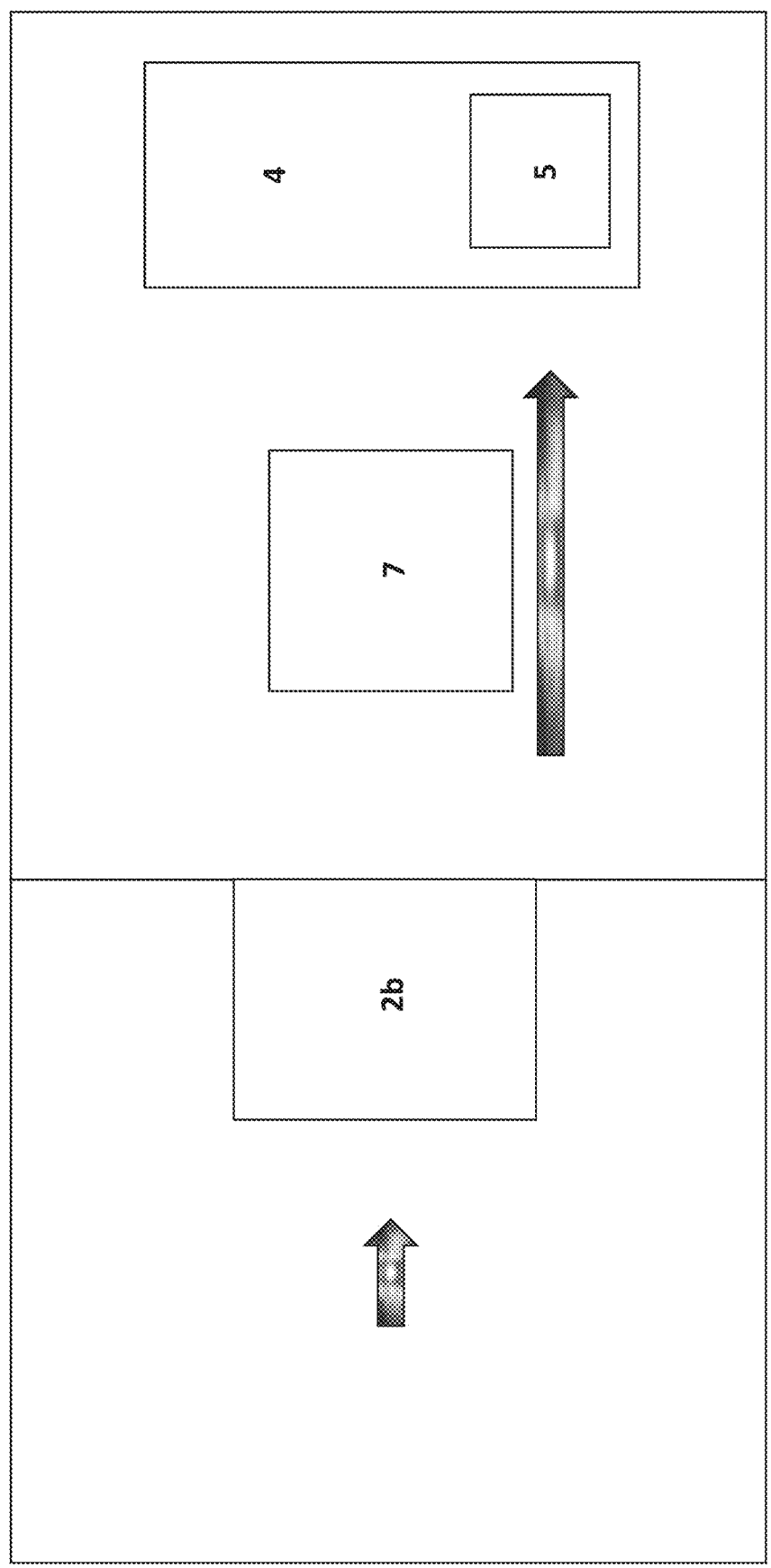
FIG. 3 shows a block diagram of a known washing, sterilization and/or aseptic transfer treatment process of a known type of alternative to that illustrated in FIGS. 1 and 2.
Figure 4:
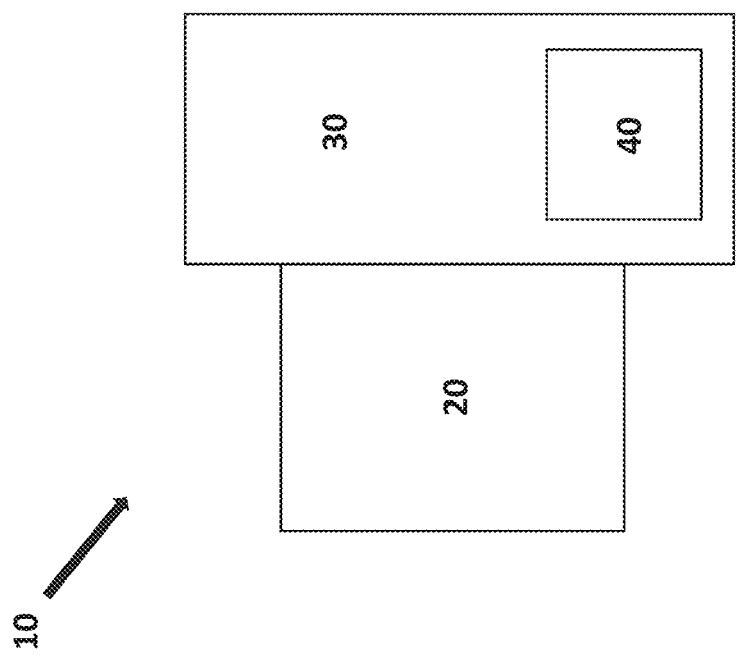
FIG. 4 shows a block diagram of an apparatus for filling containers in a sterile environment according to an embodiment of the invention.
Figure 5:
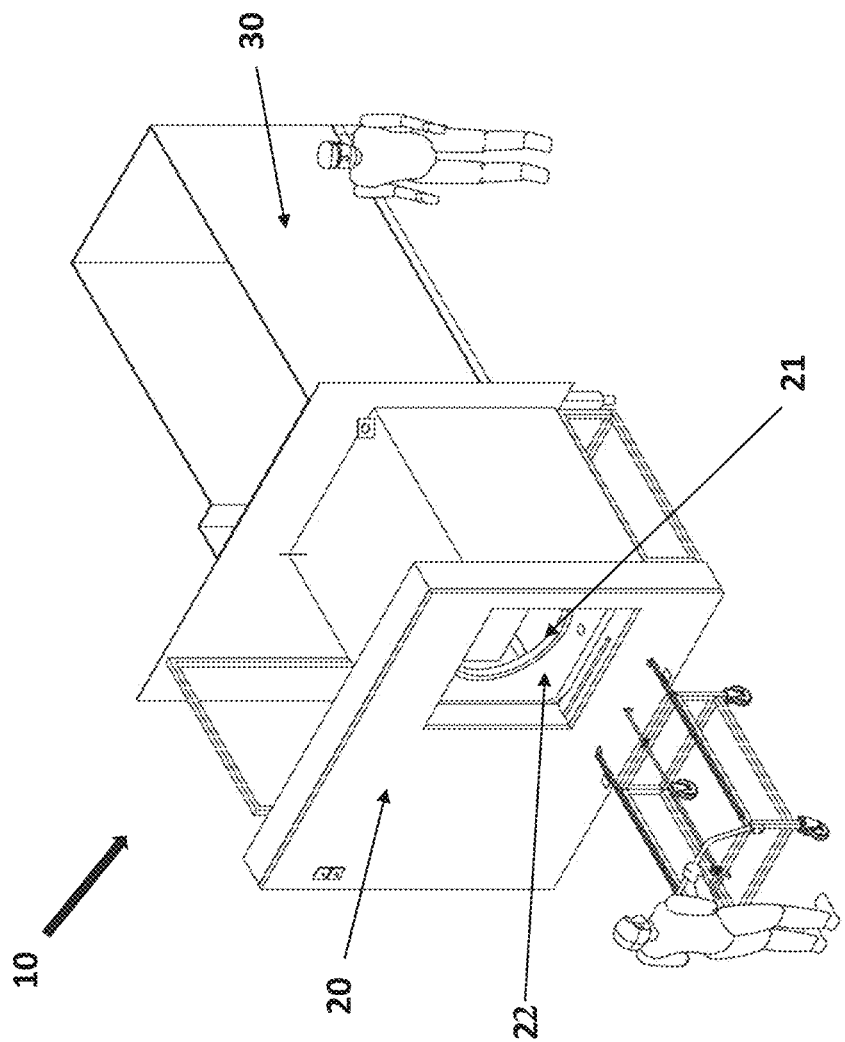
FIGS. 5 and 6 show a detail of the apparatus of FIG. 4.
Figure 6:
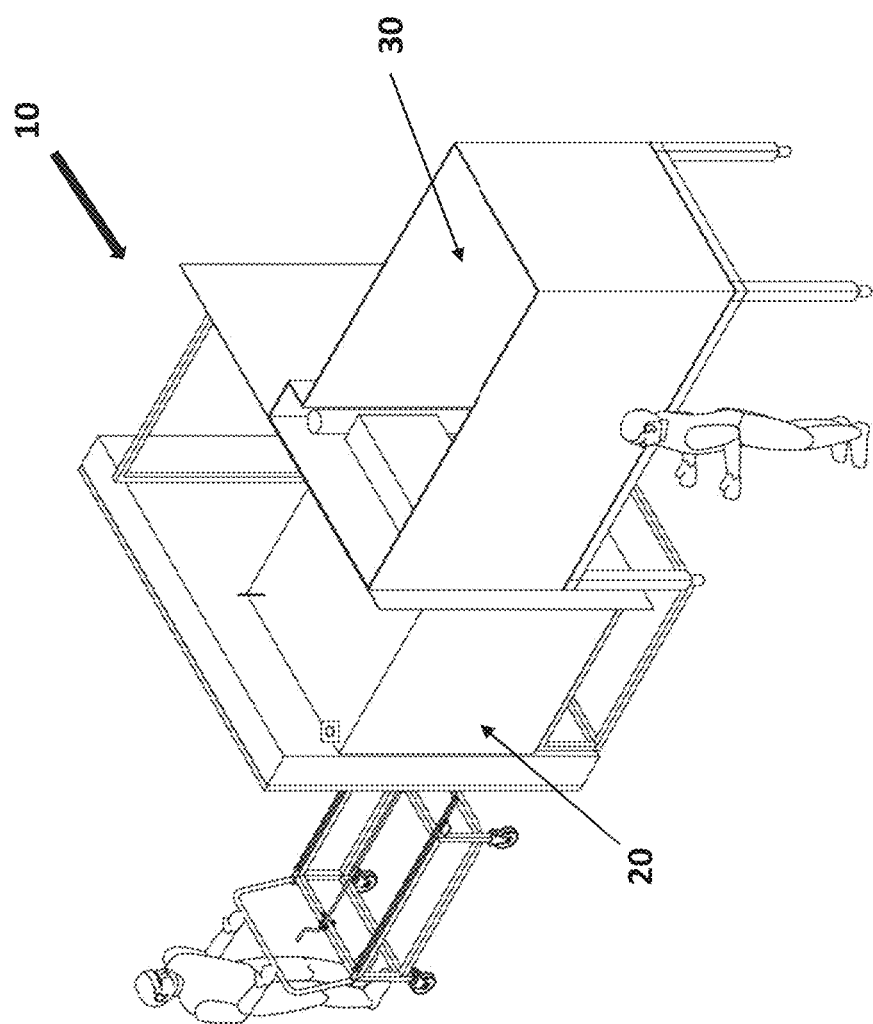
Figure 8:
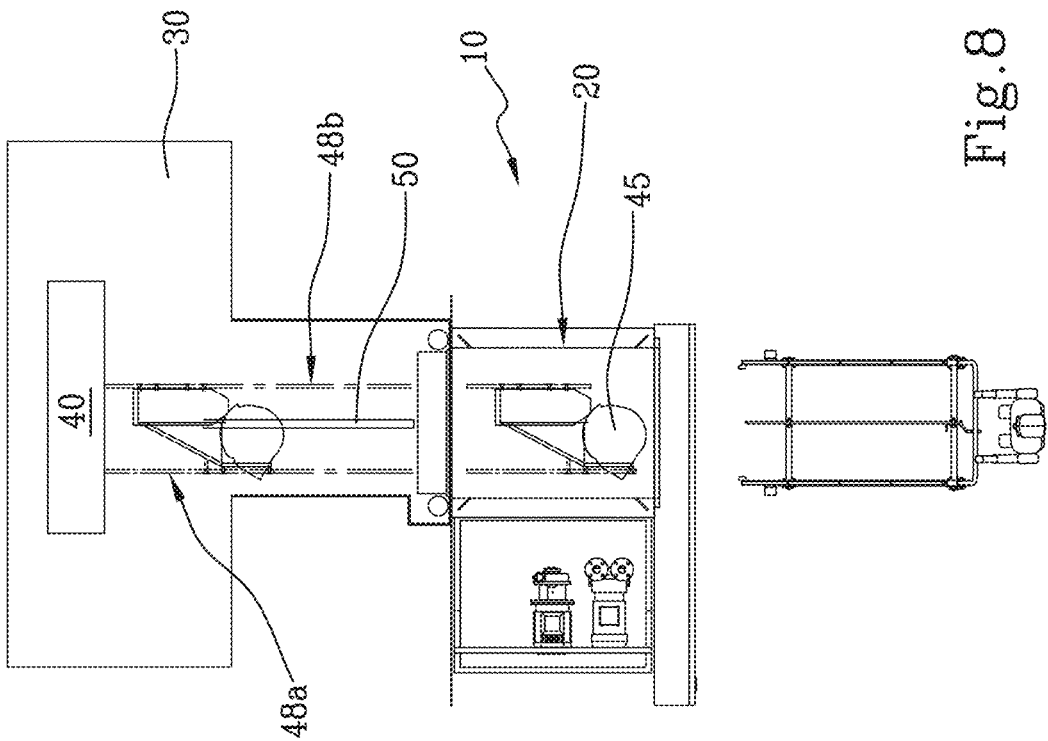
FIGS. 7 and 8 show two examples of aseptic transfer inside the apparatus of FIG. 4.
Figure 7:
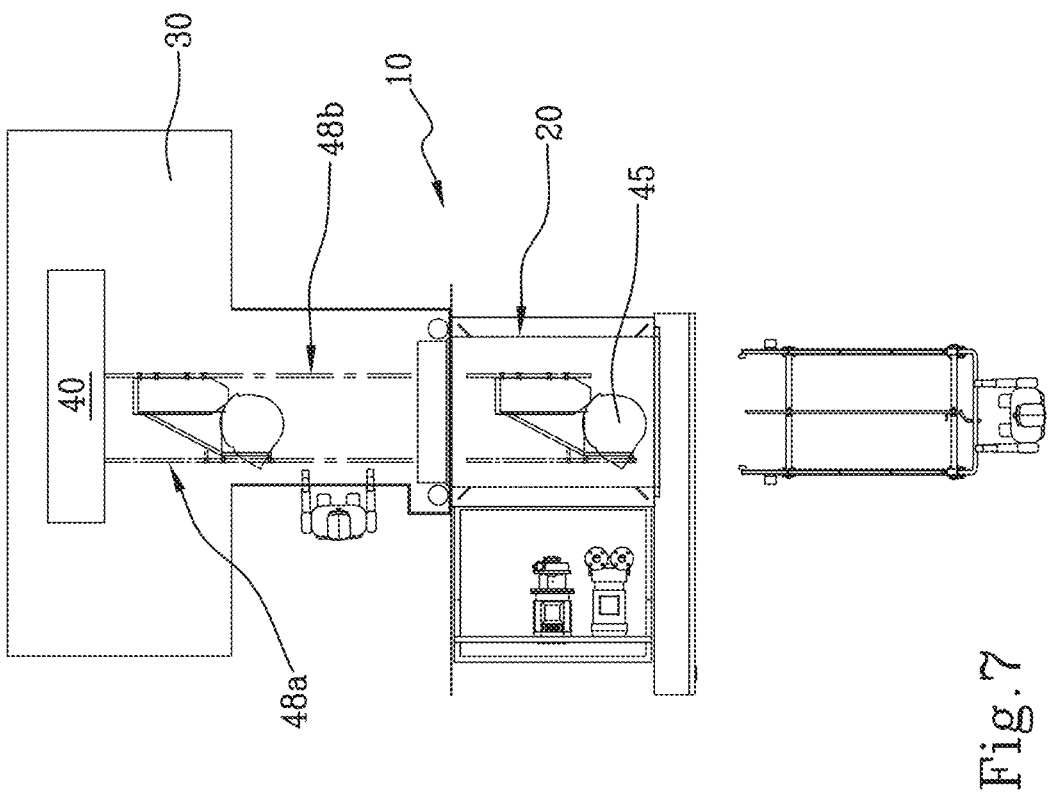

With reference to FIG. 4, an apparatus 10 for filling containers in a sterile environment according to the present invention is shown.

The apparatus 10 for filling containers in a sterile environment comprises therein a filling unit 40 configured to fill various types of containers with sterilized liquids or powders in a sterile environment. Furthermore, the filling unit 40 comprises interchangeable parts characteristic of each production run.

In particular, the interchangeable machine parts characteristic of each production run may be, for example, liquid container filling needles, feed systems, rubber stoppers, material storage reservoirs, powder dosing systems, etc.

The filling unit 40 is contained inside a protection system 30.

The apparatus 10 further comprises a washer sterilizer 20 configured to wash, sterilize, decontaminate, dry in one single process the interchangeable parts of the filling unit 40 before each run for filling the unit 40.

It should be noted that the washer sterilizer 20 is also configured to wash and/or sterilize other elements, such as the containers themselves.

The washer sterilizer 20 according to the present invention is directly coupled to the insulator 30 and is configured to aseptically transfer the interchangeable parts directly inside the filling unit 40.

Thereby it is avoided to have to bag in a special bagging unit, transfer, sterilize and extract the parts of the filling machine from the bags, thus reducing production costs and the number of machines and avoiding possible contamination.

Furthermore, having a single filling machine configured to perform all the operations necessary for a given production run reduces the production space required.

Preferably, the washer sterilizer 20 is coupled to a protection system or insulator 30 of the filling unit 40.

The protection system 30 is a system configured to maintain a class A environment in a specific area. The protection is ensured by physical and aerodynamic barriers.

By separating the filling area from the operators, these special insulators allow filling operations to be carried out, ensuring the total protection of the products and the operator without having to resort to sterile rooms.

Depending on the specific needs of the process, these aseptic systems can be easily integrated with mills, micronizers, dryers or other process instrumentation and find applicability in aseptic filling lines, sterility tests and reactors.

The protection system 30 of the filling line or unit 40 can be, by way of non-limiting example, an insulator, a RABS ("Restricted Area Barrier System") or any other system which allows activities under controlled contamination conditions.

The protection system 30 of the filling line 40 is configured to insulate the filling line 40 from each contact with an operator and from the external environment.

The washer sterilizer 20 comprises therein a rotating basket 21 configured to contain the interchangeable parts of the filling unit 40 to be washed and/or sterilized. The rotating basket 21 is housed inside a chamber 22 of the washer sterilizer 20.

The rotating basket 21 allows the load rotation (e.g., the parts of the machine to be washed and sterilized) around an axis parallel to the loading/unloading direction of the washer sterilizer 20.

Preferably, the rotating basket 21 of the washer sterilizer 20 is arranged so as to allow an immersion and/or bubbling washing associated to the load rotation present in the basket 21. The chamber 22 of the washer sterilizer 20 is partially or wholly filled with a liquid. For example, water.

Alternatively or in addition to the presence of the liquid in the chamber 22, the washer sterilizer 20 is blown with air and/or vapour.

The washed and sterilized interchangeable parts characteristic of each production run or assembly 45 can be extracted from the washer sterilizer 20 and installed inside the filling unit 40 (of which they are removably part) by a completely manual transfer or a completely automatic transfer.

Furthermore, mixed manual/automatic transfer systems are always possible by combining parts of the two main modes. In both transfer systems, the assembly 45 slides on specially made guides 48a, 48b.

Specific construction details are made from time to time based on the assembly 45 to be treated and the filling unit 40 for which it was designed.

In manual transfer mode, after activating the door opening command, an operator manually extracts the assembly 45 from the washer sterilizer 20, with or without the aid of a tool, and brings it to the connection position inside the filling unit 40.

The filling unit 40 will be provided with suitable connections and will make the assembly 45 integral with the line 40 itself.

The operator acts with gloves insulated from the units 30, 40 by the separation wall of the containment system 30.

The interchangeable parts 45 are provided with sliding means configured to slide on the guides 48a, 48b and are manually slid by the operator (wearing the gloves), from the outside of the apparatus 10.

The transfer of the interchangeable parts can occur manually and individually, from the outside of the protection system 30 and the apparatus 10, installing them on the unit 40 to other more complex solutions where the pieces are housed in special frames already configured according to the assembly which the operator always installs manually or with the aid of servo systems installed on the unit 40.

In automatic transfer mode, after activating the door opening command, the operator activates the automatic extraction commands of the assembly 45. An extraction bar 50 enters the washer sterilizer 20, engages the assembly 45 and places it at the connection point of the line. The line will be provided with suitable connections and will make the assembly 45 integral with the line itself.

In automatic transfer mode, the operator never acts with gloves on the assembly 45 or other part of the system.

In the automatic transfer mode, the interchangeable parts 45 are provided with sliding means configured to slide on the guides 48a, 48b and are slid by the extraction bar 50.

In both transfer modes of the assembly 45 described above, there will never be an operator inside the apparatus 10, thus preserving the complete sterility inside the same.

It is clear that the specific features are described in relation to different embodiments of the invention with an exemplary and non-limiting intent.

Obviously a person skilled in the art can make further modifications and variants to the present invention, in order to satisfy contingent and specific needs. For example, the technical features described in relation to an embodiment of the invention can be extrapolated therefrom and applied to other embodiments of the invention. Such modifications and variations are moreover embraced within the scope of the invention as defined by the following claims.

The invention claimed is:

1. An apparatus for filling containers in a sterile environment, comprising:
   a filling unit
      configured to fill containers with sterilized liquids or powders in a sterile environment, said filling unit comprising interchangeable parts characteristic of each production run;
   a washer sterilizer configured to wash, sterilize, decontaminate, dry in one single process said interchangeable parts of the filling unit before each run for filling the unit;
   wherein the washer sterilizer is directly coupled to the filling unit and is configured to transfer aseptically said interchangeable parts directly to the filling unit;
   wherein the washer sterilizer comprises a rotating basket configured to contain said interchangeable parts of the filling unit and the rotating basket allows the load rotation around an axis parallel to the direction of loading/unloading of the washer sterilizer.

2. The apparatus according to claim 1, wherein the washer sterilizer (20) is coupled to the filling unit by means of a protection system interposed between said washer sterilizer and said filling unit.

3. The apparatus according to claim 2, the protection system being configured to insulate the filling unit from any contact with an operator.

4. The apparatus according to claim 3, wherein the protection system of the filling unit is an insulator, a closed RABS or an open RABS.

5. The apparatus according to claim 1, wherein the rotating basket of the washer sterilizer is arranged so as to allow an immersion and/or bubbling washing associated to the load rotation of the rotating basket.

6. The apparatus according to claim 1, wherein the washer sterilizer comprises an internal chamber configured to be partially or wholly filled with a liquid.

7. The apparatus according to claim 6, wherein the internal chamber of the washer sterilizer is blown with air or vapour.

* * * * *